United States Patent [19]

Thorwart et al.

[11] Patent Number: 4,940,790
[45] Date of Patent: Jul. 10, 1990

[54] 5-(3-ALKYL-5-TERT.BUTYL-4-HYDROXY-PHENYL)-2-AMINO-6H-1,3,4-THIADIAZINES

[75] Inventors: Werner Thorwart, Hochheim am Main; Ulrich Gebert, Kelkheim; Rudolf Schleyerbach, Hofheim am Taunus; Robert R. Bartlett, Darmstadt, all of Fed. Rep. of Germany

[73] Assignee: Hoechst Aktiengesellschaft, Frankfurt am Main, Fed. Rep. of Germany

[21] Appl. No.: 149,601

[22] Filed: Jan. 28, 1988

[30] Foreign Application Priority Data

Jan. 30, 1987 [DE] Fed. Rep. of Germany ....... 3702756

[51] Int. Cl.$^5$ ............................................. C07D 285/16
[52] U.S. Cl. ......................................................... 544/8
[58] Field of Search ........................... 514/222.5; 544/8

[56] References Cited

U.S. PATENT DOCUMENTS 4,289,767  1/1981  Jones et al. ........................... 424/246

FOREIGN PATENT DOCUMENTS

DE-
OS3031703  3/1981  Fed. Rep. of Germany .
DD-PS
220311  3/1985  German Democratic Rep. .
88889/74  8/1974  Japan .

OTHER PUBLICATIONS

K. Brune, Eur. J. Rheumatol, Inflam., vol. 5 (1982), pp. 335–349.
P. K. Bose, Quart. J. Ind. Chem. Soc., vol. 2 (1925), pp. 95–114.
H. Beyer et al., Liebigs Ann. Chem., vol. 741 (1970), pp. 45–54.
H. Beyer et al., Quart. Rep. Sulfur Chem., vol. 5 (1970), pp. 177–189.
R. R. Schmidt and H. Huth, THL Tetrahedron Letters, No. 1 (1975), pp. 33–36.
J. Y. Postovskii et al., C. A., vol. 85 (1976), p. 521, ref. No. 85:177376h.
W. D. Pfeiffer et al., Z. Chem., vol. 17 (1977), pp. 218–220.
R. E. Busby and T. W. Dominey, J. Chem., Soc. Perkin (II) (1980), pp. 890–899.

Primary Examiner—John M. Ford
Attorney, Agent, or Firm—Finnegan, Henderson, Farabow, Garrett, and Dunner

[57] ABSTRACT

Novel 5-(3-alkyl-5-tert.butyl-4-hydroxyphenyl)-2-amino-6H-1,3,4-thiadiazines of the general formula I

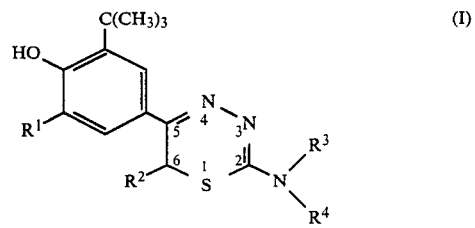

in which
$R^1 = C_1-C_4$-alkyl,
$R^2 = H$ or $C_1-C_3$-alkyl
$R^3$ and $R^4$ = independently of one another, optionally substituted and optionally O- or S-interrupted alkyl, alkenyl or alkynyl groups, it being possible for one of the two radicals to also be H,
or $R^3 + R^4$ together with the nitrogen atom to which they are bound, may denote an optionally substituted 4- to 7-membered ring which optionally contains a further heteroatom (O, S or N), and the physiologically acceptable acid-addition salts thereof. The compounds are primarily suitable for prevention and treatment of inflammatory—in particular inflammatory rheumatic—disorders and/or pain.

3 Claims, No Drawings

5-(3-ALKYL-5-TERT.BUTYL-4-HYDROXY-PHENYL)-2-AMINO-6H-1,3,4-THIADIAZINES

The present invention relates to novel 5(3-alkyl-5-tert. butyl-4-hydroxyphenyl)-2-amino-6H-1,3,4-thiadiazines, a process for the preparation thereof, and the use thereof as active compounds in medicaments for treating inflammatory disorders, in particular inflammatory rheumatic disorders, and pain.

The non-steroidal antiphlogistics preferably employed hitherto in rheumatherapy are almost exclusively relatively strong cyclooxygenase inhibitors, which inhibit endogenic degradation of arachidonic acid into inflammation- and pain-promoting prostaglandins. However, a number of serious side effects are causally associated with excessive inhibition of cyclooxygenase activity, such as gastrointestinal complaints, kidney dysfunctions and allergic reactions (e.g. skin allergies and asthmatic attacks), which frequently require termination of the therapy, in particular in the case of the long-term treatment which is usually necessary (cf. K. Brune, Eur. J. Rheumatol. Inflam. 5 (1982), pp. 335–349).

A further disadvantage of these classical non-steroidal antiphlogistics which is causally associated with the described mechanism of action is that although they allow elimination or alleviation of the pain, inflammation and swelling symptoms, they do not affect the pathological processes which are partly involved in causing the advanced course of the inflammatory rheumatic disorders.

There is thus an urgent demand for therapeutically useful antirheumatics which, due to a more favorable profile of action, differ advantageously from the known non-steroidal antiphlogistics through better tolerance on the one hand and more specific engagement against the advanced course of the rheumatic pathological process on the other hand. Promising starting points for such medicaments are pharmaceuticals which have an antiphlogistic and analgesic action and which engage to an increased extent in the alternative route of arachidonic acid degradation, for example by inhibiting 5-lipoxygenase and thus suppressing excessive formation of pro-inflammatory leukotrienes and deactivate the highly reactive oxygen radicals which, as inflammation mediators, perpetually maintain cell and tissue destruction in the inflammatory rheumatic joints and thus open up the possibility of drug therapy in the vicious circle of rheumatic disorders.

Surprisingly, it has now been found that, by introducing certain 3-alkyl-5-tert.butyl-4-hydroxyphenyl radicals into the 5-position of optionally 6-substituted 2-amino-6H-1,3,4-thiadiazines, novel compounds are obtained which, due to their pharmacological properties, meet the demands set above and, accordingly, are highly suitable for treatment of rheumatic disorders.

In contrast to the known non-steroidal antiphlogistics, the compounds, which are also well tolerated gastrally, also inhibit the arachidonic acid-degrading enzyme 5-lipoxygenase even in therapeutically relevant doses. The ability of the compounds to deactivate oxygen cadicals is apparent, for example, in the model of (R) Adriamycin (Messrs. Farmitalia) induced inflammation.

5-Phenylated 2-amino-6H-1,3,4-thiadiazines have already been described many times in the literature (P. K. Bose, Quart. J. Ind. Chem. Soc. 2 (1925), pp. 95–114; H. Beyer et al., Liebigs Ann. Chem. 741 (1970), pp. 45–54; H. Beyer, Quart. Rep. Sulfur Chem. 5 (1970), pp. 177–189; R. R. Schmidt and H. Huth, THL 1975, pp. 33–36; J. Y. Postovskii et al., Khim. Geterotsikl. Soedin. 1976, pp. 1051–1055, ref. in Chem. Abstr. Vol. 85 (1976), p. 521 Ref. No. 85:177376h; W. D. Pfeiffer et al., Z. Chem. 17 (1977), pp 218–220, and R. E. Busby and T. W. Dominey, J. Chem. Soc. 1980, pp 890–899), of which, however, no pharmacologic properties are known. In contrast, German Offenlegungsschrift No. 3,031,703 reports certain 5-(chlorophenyl)-2-amino-6H-1,3,4-thiadiazines which are ascribed a spasmolytic and anxiolytic action. Furthermore, DD Patent 220,311 discloses, inter alia, 5-phenyl-6H-1,3,4-thiadiazines which have the very specific N-methyl-N-(1-hydroxy-1-phenylprop-2-yl)-amino radical in the 2-position and are said to have a spasmolytic activity.

By contrast, the present invention relates to novel 2-amino-6H-1,3,4-thiadiazines which carry, as an essential pharmacophoric group, a 3-alkyl-5-tert.butyl-4-hydroxyphenyl radical in the 5-position and, if appropriate, a further substituent in the 6-position. Due to their abovementioned pharmacological properties, the compounds according to the invention are suitable for use in medicaments, in particular in those which are indicated in inflammatory rheumatic disorders and attacks of pain.

The invention thus relates to 5-(3-alkyl-5-tert.butyl-4-hydroxyphenyl)-2-amino-6H-1,3,4-thiadiazines of the general formula I

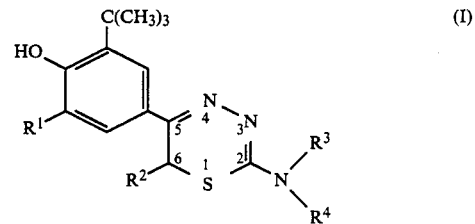

in which $R^1$ denotes a straight-chain or branched alkyl group having 1 to 4 carbon atoms, $R^2$ denotes a hydrogen atom or an alkyl radical having 1 to 3 carbon atoms, $R^3$ and $R^4$, independently of one another, represent a straight-chain or branched ($C_1$–$C_6$)alkyl, ($C_3$–$C_6$)-alkenyl or ($C_3$–$C_6$)alkynyl group which can be substituted by phenyl or halogen, ($C_1$–$C_3$)alkyl- or ($C_1$–$C_3$) alkoxy-substituted phenyl, hydroxyl or ($C_1$–$C_4$)acyloxy and/or whose C—C sequence may be interrupted by a heteroatom in the form of oxygen or sulfur, it also being possible for one of the two radicals to denote a hydrogen atom, or $R^3$ and $R^4$ together with the nitrogen atom to which they are bound, form a 4- to 7-membered ring which may be monosubstituted or polysubstituted by ($C_1$–$C_4$)alkyl and/or contains, in place of one of the ring carbon atoms, a further heteroatom in the form of oxygen, sulfur or nitrogen, it also being possible for the latter to carry an alkyl group having 1 to 3 carbon atoms or a phenyl radical in place of hydrogen, and the physiologically acceptable acid-addition salts thereof.

Preference is given here to compounds of the formula I, and the salts thereof, in which $R^1$ denotes tert.butyl or methyl or $R^2$ represents hydrogen or methyl. Preferred compounds are also those in which $R^3$ and $R^4$, independently of one another, represent a straight-chain or branched $(C_1-C_3)$alkyl or $(C_3-C_4)$alkenyl group, which may be substituted by optionally substituted phenyl or hydroxyl or whose C—C sequence may be interrupted by an oxygen atom, it also being possible for one of the two radicals to denote a hydrogen atom, or $R^3$ and $R^4$, together with the nitrogen atom to which they are bound, form a 5- or 6-membered ring which may be substituted by a $(C_1-C_2)$alkyl radical or contains, in place of one of the ring carbon atoms, a further heteroatom in the form of oxygen or nitrogen, it also being possible for the latter to carry an alkyl group having 1 or 2 carbon atoms in place of hydrogen. Of these compounds, those should in turn be particularly emphasized in which $R^1$ denotes a tert.butyl radical and simultaneously $R^2$ represents hydrogen or methyl and $R^3$ and $R^4$, independently of one another, denote a straight-chain or branched $(C_1-C_3)$alkyl or $(C_3-C_4)$alkenyl group which may be substituted by phenyl, it also being possible for one of the two radicals to be a hydrogen atom, or $R^3$ and $R^4$, together with the nitrogen atom to which they are bound, form a piperidine, 4-methylpiperidine, piperazine or 4-methylpiperazine ring.

Methyl, ethyl, n-propyl, isopropyl, n-butyl, isobutyl, sec.butyl and tert.butyl are suitable alkyl radicals for the $R^1$ group, methyl, ethyl, n-propyl and isopropyl for the $R^2$ group and methyl, ethyl, propyl, isopropyl, n-butyl, isobutyl, sec.butyl, tert.butyl and the various pentyl and hexyl radicals, for example neopentyl, for the $R^3$ and/or $R^4$ groups Further suitable groups for the $R^3$ and/or $R^4$ radicals are, for example, allyl, the various butenyl, pentenyl and hexenyl radicals, propargyl, the various butynyl, pentynyl and hexynyl radicals, 2-hydroxyethyl, methoxyethyl, ethoxyethyl, methylthioethyl, ethylthioethyl, optionally substituted benzyl and phenethyl, and also, including the nitrogen atom to which they are bound, the cyclic systems, such as pyrrolidine, piperidine, 4-methylpiperidine, morpholine, thiomorpholine, piperazine, 4-methyl and 4-phenylpiperazine.

The invention furthermore relates to a process for the preparation of the novel 5-(3-alkyl-5-tert.butyl-4-hydroxyphenyl)-2-amino-6H-1,3,4-thiadiazines of the formula I and the physiologically acceptable acid-addition salts thereof, wherein a 2-halo-1-phenylalkanone of the formula II

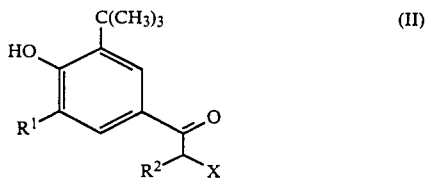

is reacted with a thiosemicarbazide of the formula III

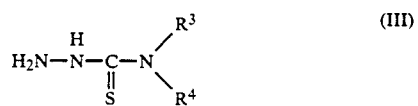

where $R^1$, $R^2$, $R^3$ and $R^4$ have the abovementioned meanings and X represents a halogen atom, preferably chlorine or bromine, to give the compounds of the formula I according to the invention, and the latter are either isolated in free form or converted into physiologically acceptable addition salts by means of suitable acids.

Suitable for the preparation of acid-addition salts are, for example, mineral acids, such as hydrobromic acid, hydrochloric acid, sulfuric acid or phosphoric acid; organic acids, such as acetic acid, lactic acid, maleic acid, fumaric acid, oxalic acid, tartaric acid, citric acid or gluconic acid; or other physiologically acceptable acids, such as sulfonic acids, for example benzenesulfonic acid, p-toluenesulfonic acid, methanesulfonic acid, trifluoromethylsulfonic acid and cyclohexylamidosulfonic acid.

The 2-halo-1-phenyl alkanones of the formula II used as starting materials for the one-step process are known from the literature or can easily be prepared from 1-(3-alkyl-5-tert.butyl-4-hydroxyphenyl)alkanones through reaction with a suitable halogenating agent by the methods described in Houben-Weyl Vol. V/4 (1960), pp. 171–189. Suitable compounds II which may be mentioned are, for example, 2-bromo-1-(3,5-di-tert.butyl-4-hydroxyphenyl)-ethanone and 2-bromo-1-(5-tert.butyl-3-methyl-4-hydroxyphenyl)-ethanone, which can be prepared by halogenating the correspondingly substituted 1-phenyl alkanones using elemental bromine or using copper(II)bromide by the process of L. C. King and G. K. Ostrum, J. Org. Chem. 29 (1964), pp. 3459–3461.

For obtaining those compounds of the formula II in which X represents a chlorine atom, elemental chlorine or sulfuryl chloride, in particular, are suitable, the latter preferably being brought to reaction with the appropriate 1-phenyl alkanones at temperatures between about 10° and 30° C. in the presence of inert solvents, such as, for example, methylene chloride or chloroform. A further preparation process comprises Friedel-Crafts acylation of 2-alkyl-6-tert.butylphenols, preferably using chloroacetyl chloride in the presence of Lewis acids, such as, for example aluminum chloride or boron trifluoride.

The 4-monosubstituted or 4,4-disubstituted thiosemicarbazides of the formula III which are likewise employed as starting materials are mostly known from the literature or can be prepared by the methods described in Houben-Weyl, Vol. E 4, pp. 506–515, and by K. A. Jensen et al., Acta Chem. Scand. 22 (1968), pp. 1–50. Thus, the thiosemicarbazides III in which one of the radicals $R^3$ and $R^4$ denotes hydrogen can advantageously be obtained by adding hydrazine to isothiocyanates, whereas the 4,4-disubstituted thiosemicarbazides III are preferably prepared by reacting the appropriately N,N-di-substituted thiocarbamoyl chlorides with hydrazine. In order to avoid interfering side reactions, these preparations are advantageously carried out in an aprotic solvent, such as, for example, chloroform, tetrachloromethane or diethyl ether, at reaction temperatures below about 10° C. (D. L. Klayman et al., J. Med. Chem. 22 (1979), pp. 1367–1373).

A further process which allows the preparation of the 4-monosubstituted and 4,4-disubstituted thiosemicarbazides proceeds from the appropriately N-substituted thiocarbamoyl mercaptoacetic acids of the formula IV

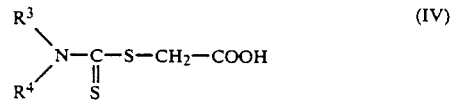

which can be converted into the compounds III by means of hydrazine in the presence of dilute bases, such as, for example, sodium hydroxide or potassium hydroxide, on refluxing for up to several days (K. A. Jensen, J. prakt. Chem. 159 (1941), pp. 189–192).

The reaction of 2-halo-1-phenylalkanones II with the thiosemicarbazides III is expediently carried out using equimolar amounts of the two reactants in a solvent or distributing agent which is inert towards the reactants. Suitable for this purpose are, in particular, lower alcohols, such as methanol, ethanol, n-propanol, isopropanol and the various butanols, or ethyl acetate, and mixtures thereof, but preferably ethanol. The reaction is generally carried out at temperatures between about $-20°$ C. and the boiling point of the particular reaction medium used, but preferably at about $20°$ to $70°$ C. Depending on the reactivity of the reactants, the type of the reaction medium and the reaction temperature used, reaction time can be between about 5 minutes and 2 hours. The final products of the formula I usually crystallize in analytically pure form on slow cooling of the reaction mixture, so that further purification operations are generally superfluous. However, if spontaneous crystallization does not occur, it is advisable to evaporate the reaction mixture to dryness under reduced pressure and to digest the residue which remains thoroughly at room temperature in a suitable solvent or distributing agent, for example a carboxylate, such as ethyl acetate; a ketone, such as acetone or methyl ethyl ketone; an ether, such as diisopropyl ether or methyl tert.butyl ether; or mixtures thereof. The crystalline product produced during this operation is purified either by recrystallization or by repeated digestion in the same solvent or distributing agent, by boiling briefly, cooling, filtering off under suction and drying in a drying cabinet.

The preparation from the 4-monosubstituted thiosemicarbazides III of the compounds I according to the invention which have a hydrogen atom in the position of $R^3$ or $R^4$ proceeds particularly homogeneously if the thiosemicarbazides are employed for the reaction in the form of their salts, for example their hydrochlorides.

Due to their valuable pharmacological properties with, at the same time, excellent tolerance, the 5-(3-alkyl-5-tert.butyl-4-hydroxyphenyl)-2-amino-6H-1,3,4-thiadiazines of the formula I and the physiologically acceptable acid-addition salts thereof are particularly suitable for use as active compounds in medicaments, in particular in those for treating inflammatory rheumatic disorders and attacks of pain. They can be administered either alone, for example in the form of microcapsules, in mixtures with one another or in combination with suitable adjuvants and/or excipients.

The invention thus also relates to medicaments which comprise at least one compound of the formula I, if appropriate in the form of one of its acid-addition salts, or contain at least one of these active compounds in addition to pharmaceutically suitable and physiologically acceptable excipients, diluents and/or other adjuvants.

The medicaments according to the invention can be administered orally, topically, rectally or, if appropriate, also parenterally, oral administration being preferred.

Suitable solid or liquid galenic formulations are, for example, granules, powders, coated tablets, tablets, (micro)capsules, suppositories, syrups, elixirs, suspensions, emulsions, drops or injectable solutions, and also preparations having a protracted release of active compound, in the production of which adjuvants, such as excipients, disintegrants, binders, coating agents, swelling agents, glidants, lubricants, flavors, sweeteners or solubilizers are usually used. Frequently used adjuvants which may be mentioned are, for example, magnesium carbonate, titanium dioxide, lactose, mannitol and other sugars, talc, lactalbumin, gelatin, starch, cellulose and derivatives thereof, animal and vegetable oils, polyethylene glycols and solvents, such as, for example, sterile water and monohydric or polyhydric alcohols, for example glycerol.

The pharmaceutical preparations are preferably produced and administered in dosage units, each unit containing as active component a certain dose of at least one compound of the formula I and/or at least one corresponding acid-addition salt. In the case of solid dosage units, such as tablets, capsules, coated tablets or suppositories, this dose can be up to about 800 mg, but preferably about 100 to 500 mg.

For treatment of an adult patient suffering from inflammatory rheumatic disorders and from pain, daily doses from about 100 to 2000 mg of active compound, preferably about 300 to 1000 mg, —depending on the activity in humans of the compounds of the formula I and/ or of the corresponding acid-addition salts—are indicated in the case of oral administration. Under certain circumstances, however, higher or lower daily doses may be appropriate. Administration of the daily dose can take place by means of a single administration in the form of a single dosage unit or several smaller dosage units, or alternatively by multiple administration of divided doses at certain intervals.

Finally, in the production of the abovementioned galenic formulations, the compounds of the formula I and the corresponding acid-addition salts can also be formulated together with other suitable active compounds, for example antiuricopathics, thrombocyte-aggregation inhibitors, other analgesics and other steroidal or non-steroidal antiphlogistics.

The structure of all the compounds described below has been confirmed by elemental analysis and IR and $^1$H-NMR spectra. The compounds of the formula I prepared according to Examples 1 to 4 below and the compounds prepared in an analogous fashion are collated in table 1.

EXAMPLE 1:

5-(3,5-di-tert.butyl-4-hydroxyphenyl)-2-dimethylamino-6H-1,3,4-thiadiazine hydrobromide (a)

2-bromo-1-(3,5-di-tert.butyl-4-hydroxyphenyl)-ethanone 206 g (0.83 mol) of 1-(3,5-di-tert.butyl-4-hydroxyphenyl)ethanone were dissolved in 415 ml of methylene chloride while stirring, the solution was heated to boiling, and 144 g (0.9 mol) of bromine were added dropwise over the course of 30 minutes. The mixture was then refluxed for a further 2 hours and cooled, 400 ml of water were added, and the organic phase was separated off and dried over sodium sulfate. After the solvent had been removed under reduced pressure, the solid crude product obtained was recrystallized from 540 ml of methylcyclohexane.

Yield: 191 g (67% of theory). Melting point: $105°$–$108°$ C. $C_{16}H_{23}BrO_2$ (MW = 327.3).

(b)
5-(3,5-di-tert.butyl-4-hydroxyphenyl)-2-dimethylamino-6H-1,3,4-thiadiazine hydrobromide 196.4 g (0.6 mol) of 2-bromo-1-(3,5-di-tert.butyl-4-hydroxyphenyl)-ethanone from step (a) and 59.6 g (0.5 mol) of 4,4-dimethylthiosemicarbazide were suspended in 1500 ml of ethanol and slowly heated to 70° C. while stirring, a clear solution being produced. The solution was stirred at this temperature for 10 minutes and then cooled, and the solvent was removed under reduced pressure. Washing the residue, produced as an oil, by stirring with 500 ml of ethyl acetate produced a batch of crystals, which was again briefly heated to boiling in 500 ml of ethyl ester. The crystalline product was filtered off, washed with 150 ml of ethyl acetate and dried in a vacuum cabinet.

Yield: 165.5 g (77.3% of theory). Melting point: 256°–257° C. $C_{19}H_{30}BrN_3OS$ (MW=428.4).

Analysis: Calculated: C 53.27%; H 7.06%; Br 18.65%; N 9.81%; S 7.48%. Found: C 53.29%; H 7.11%; Br 18.10%; N 9.77%; S 7.60%.

EXAMPLE 2:
5-(3,5-di-tert.butyl-4-hydroxyphenyl)-2-(4-methyl piperidino)-6H-1,3,4-thiadiazine hydrobromide (a) (4-methylpiperidino)-thiocarbohydrazide A solution of 35.5 g (0.2 mol) of (4-methylpiperidino)-thiocarbonyl chloride in 70 ml of chloroform was added dropwise over the course of 2 hours while stirring and with ice cooling to 100.1 g of 99% strength hydrazine hydrate in 50 ml of chloroform. After stirring for a further 2 hours, the reaction mixture was evaporated to dryness under reduced pressure, and the oily residue was washed by stirring in 200 ml of diisopropyl ether. The crystals formed during this operation were recrystallized from ethyl acetate.

Yield: 21.5 g (62% of theory). Melting point: 113°–115° C. $C_7H_{15}N_3S$ (MW=173.3).

(b)
5-(3,5-di-tert.butyl-4-hydroxyphenyl)-2-(4-methylpiperidino)-6H-1,3,4-thiadiazine-hydrobromide 18.0 g (0.055 mol) of 2-bromo-1-(3,5-di-tert.butyl-4-hydroxyphenyl)-ethanone of Example 1(a) and 8.7 g (0.05 mol) of (4-methylpiperidino)-thiocarbohydrazide from step (a) were dissolved in 150 ml of ethanol, and the solution was heated to boiling for 10 minutes. Workup took place under the conditions described in Example 1(b).

Yield: 17.4 g (72% of theory). Melting point: 190°–193° C. $C_{23}H_{36}BrN_3OS$ (MW=482.5).

Analysis: Calculated: C 57.26%; H 7.52%; Br 16.56%; N 8.71%; S 6.65%. Found: C 57.02%; H 7.61%; Br 16.51%; N 8.73%; S 6.77%.

EXAMPLE 3:
5-(5-tert,butyl-3-methyl-4-hydroiyphenyl)-2-dimethylamio-6H-1,3,4-thiadiazine hydrobromide (a)
2-bromo-1-(5-tert.butyl-3-methyl-4-hydroxyphenyl)-ethanone A solution of 82.5 g (0.4 mol) of 1-(5-tert.butyl-3-methyl-4-hydroxyphenyl)-ethanone in 360 ml of chloroform was added dropwise while stirring to a suspension, heated to boiling, of 179 g (0.8 mol) of copper(II) bromide in 360 ml of ethyl acetate. The mixture was subsequently refluxed for 4 hours until the evolution of hydrogen bromide was complete. After the mixture had been cooled to room temperature, the copper salts were filtered off under suction, the filter residue was washed repeatedly with ethyl acetate, the filtrate was evaporated under reduced pressure, and the solid residue was recrystallized from cyclohexane.

Yield: 81.9 g (72% of theory). Melting point: 90°–92° C. $C_{13}H_{17}BrO_2$ (MW=285.2).

(b)
5-(5-tert.butyl-3-methyl-4-hydroxyphenyl)-2-dimethylamino-6H-1,3,4-thiadiazine hydrobromide A solution of 11.7 g (0.041 mol) of 2-bromo-1-(5-tert.butyl)-3-methyl-4-hydroxyphenyl)-ethanone from step (a) and 4.4 g (0.037 mol) of 4,4-dimethylthiosemicarbazide in 130 ml of ethanol was refluxed briefly. After cooling, the reaction mixture was worked up corresponding to Example 1(b).

Yield: 12.2 g (85.3% of theory). Melting point: 197° C. $C_{16}H_{24}BrN_3OS$ (MW=386.4).

Analysis: Calculated: C 49.74%; H 6.26%; Br 20.68%; N 10.87%; S 8.30%. Found: C 49.37%; H 6.21%; Br 20.49%; N 10.87%; S 8.00%.

EXAMPLE 4:
5-(3,5-di-tert.butyl-4-hydroxyphenyl)-2-methylamino-6H-1,3,4-thiadiazine-hydrochloride (a)
2-chloro-1-(3,5-di-tert.butyl-4-hydroxyphenyl)-ethanone 16.2 g (0.12 mol) of sulfuryl chloride in 50 ml of methylene chloride were added dropwise while stirring to a solution of 19.9 g (0.08 mol) of 1-(3,5-di-tert.butyl-4-hydroxyphenyl)-ethanone in 250 ml of methylene chloride at room temperature. After stirring for 3 hours at room temperature, the batch was washed by shaking first with water and then with a saturated sodium hydrogen carbonate solution, and the methylene chloride phase was dried over sodium sulfate and evaporated under reduced pressure.

The residue was recrystallized from 60 ml of isopropanol.

Yield: 12.7 g (56% of theory). Melting point: 120°–122° C. $C_{16}H_{23}ClO_2$ (MW=282.8).

Analysis: Calculated: C 67.95%; H 8,20%; Cl 12.54%. Found: C 67.87%; H 8.32%; Cl 12.29%.

(b)
5-(3,5-di-tert.butyl-4-hydroxyphenyl)-2-methylamino-6H-1,3,4-thiadiazine hydrochloride 10.7 g (0.038 mol) of 2-chloro-1-(3,5-di-tert.butyl-4-hydroxyphenyl)-ethanone from step (a) and 4.8 g (0.034 mol) of 4-methylthiosemicarbazide hydrochloride were dissolved in 120 ml of ethanol, and the mixture was heated to boiling for 30 minutes. After cooling, the solvent was removed by distillation under reduced pressure, and the resinous residue was dissolved in 60 ml of warm ethyl acetate. On standing, the product immediately precipitated in crystalline form, and was filtered off and recrystallized again from 150 ml of a mixture of ethyl acetate and methylene chloride (10 : 1).

Yield: 8.9 g (71% of theory). Melting point: 207°–209° C. $C_{18}H_{28}ClN_3OS$ (MW=370.0).

Analysis: Calculated: C 58.44%; H 7.63%; Cl 9.58%; N 11.36%; S 8.67%. Found: C 58.13%; H 7.72%; Cl 9.31%; N 11.22%; S 8.78%.

TABLE 1

Compounds according to formula I (cf. claim 1)

| Example | R¹ | R² | R³ | R⁴ | Melting point °C. |
|---|---|---|---|---|---|
| 1 | (H₃C)₃C— | H | —CH₃ | —CH₃ | 256–257 (hydrobromide) |
| 2 | (H₃C)₃C— | H |  | 4-methylcyclohexyl | 190–193 (hydrobromide) |
| 3 | H₃C— | H | —CH₃ | —CH₃ | 197 (hydrobromide) |
| 4 | (H₃C)₃C— | H | H | —CH₃ | 207–209 (hydrochloride) |
| 5 | H₃C— | H | H | —CH₂—CH=CH₂ | 198–200 (hydrochloride) |
| 6 | H₃C— | H | —CH₂—CH₃ | —CH₂—CH₃ | 182–184 (hydrobromide) |
| 7 | H₃C— | H | —CH₃ | —CH₂—C₆H₅ | 190–191 (hydrobromide) |
| 8 | (H₃C)₃C— | H | —CH₃ | —CH₂—CH₃ | 200 (hydrobromide) |
| 9 | (H₃C)₃C— | H | —CH₂—CH₃ | —CH₂—CH₃ | 188–190 (hydrobromide) |
| 10 | (H₃C)₃C— | H | —CH₂—CH₃ | —CH(CH₃)₂ | 179–181 (hydrobromide) |
| 11 | (H₃C)₃C— | H | —CH₂—CH₂—CH₃ | —CH₂—CH₂—CH₃ | 187–189 (hydrobromide) |
| 12 | (H₃C)₃C— | H | H | —CH₂—C₆H₅ | 223–225 (hydrobromide) |
| 13 | (H₃C)₃C— | H | —CH₃ | —CH₂—C₆H₅ | 192–194 (hydrobromide) |
| 14 | (H₃C)₃C— | H | H | —CH₂—CH=CH₂ | 193–194 (hydrobromide) |
| 15 | (H₃C)₃C— | H | H | —CH₂—CH₂—OH | 214–215 (hydrobromide) |
| 16 | (H₃C)₃C— | H | —CH₂—CH₂—O—CH₃ | —CH₂—CH₂—O—CH₃ | 151–152 (hydrochloride) |
| 17 | (H₃C)₃C— | H |  | pyrrolidinyl | 247–250 (hydrobromide) |
| 18 | (H₃C)₃C— | H |  | piperidinyl | 177–179 (hydrobromide) |
| 19 | (H₃C)₃C— | H |  | morpholinyl | 188–191 (hydrobromide) |
| 20 | (H₃C)₃C— | H |  | 4-methylpiperazinyl | 280 (Zers.) (dihydrobromide) |

TABLE 1-continued

Compounds according to formula I (cf. claim 1)

| Example | R¹ | R² | R³ | R⁴ | Melting point °C. |
|---|---|---|---|---|---|
| 21 | $(H_3C)_3C-$ | H | | 4-(piperidin-1-yl)phenyl | 188–190 (hydrobromide) |
| 22 | $(H_3C)_3C-$ | $H_3C-$ | $-CH_3$ | $-CH_3$ | 199–200 (hydrobromide) |
| 23 | $(H_3C)_3C-$ | H | H | $-CH_2-C(CH_3)_3$ | 227–229 (hydrobromide) |
| 24 | $(H_3C)_3C-$ | H | H | $-CH_2-CH_2-O-CH_3$ | 197–198 (hydrobromide) |
| 25 | $(H_3C)_3C-$ | H | H | $-CH_2-$(4-methoxyphenyl) | 208–209 (hydrobromide) |
| 26 | $(H_3C)_3C-$ | H | H | $-CH_2-$(4-chlorophenyl) | 219–220 (hydrobromide) |
| 27 | $(H_3C)_3C-$ | H | H | $-CH_2-$(4-methylphenyl) | 220–221 (hydrobromide) |
| 28 | $(H_3C)_3C-$ | H | $-CH_2-CH_2-OH$ | $-CH_2-$phenyl | 183–184 (hydrobromide) |
| 29 | $(H_3C)_3C-$ | H | H | $-CH_2-CH_2-$phenyl | 217–218 (hydrobromide) |
| 30 | $(H_3C)_3C-$ | $H_3C-$ | H | $-CH_2-CH=CH_2$ | 195–196 (hydrobromide) |
| 31 | $(H_3C)_3C-$ | $H_3C-$ | $-CH_3$ | $-CH_2-$phenyl | 146–147 (hydrobromide) |
| 32 | $(H_3C)_3C-$ | H | | thiomorpholin-4-yl | 190–191 (hydrobromide) |

Pharmacological Testing and Results

The compounds of the formula I according to the invention were tested for antiphlogistic and analgesic action, oxygen radical-deactivating potency, ulcerogenic activity and acute toxicity in the animal models described below, the antiphlogistic naproxen (2-(6-methoxy-2-naphthyl)-propionic acid), one of the first choice standard preparations in rheumotherapy, being included in the investigations as the comparison substance.

1. Adjuvant arthritis

The investigations were carried out by the method of Pearson (Arthrit. Rheum. 2 (1959), p. 44). The experimental animals used were male rats of a Wistar-Lewis strain having a body weight between 130 and 200 g. The compounds to be tested were administered orally (p. o.) once daily from day 1 to day 5 of the experiment in doses of 50 mg per kg of body weight. The animals in a control group received only the vehicle. Each preparation and control group comprised 8 animals. The criterion for action was the percentage reduction in the increase in paw volume compared to that of the untreated control group.

2. Acute gastral ulcerogenity

The investigation took place on 10 male Sprague-Dawley rats whose gastric mucous membrane had been sensitized by hunger stress. The body weight of the animals was between 200 and 300 g. While allowing free access to the drinking water, the feed was withdrawn from the animals 48 hours before administration of the test preparations until sacrifice of the animals. The rats were sacrificed 24 hours after oral substance administration, and the stomachs were removed, cleaned under running water and inspected for mucous membrane lesions. All macroscopically visible lesions were regarded as ulcers. The number of animals having ulcers was determined for each dose, and the $UD_{50}$ values, i.e. the doses at which lesions were caused in 50% of the animals, were calculated from these figures by the method of Litchfield and Wilcoxon (J. Pharmacol. Exp. Ther. 96 (1949), p. 99).

3. Acute Toxicity

The $LD_{50}$ values were determined by a standard method from the mortality occurring within 7 days in NMRI (Naval Medical Research Institute) mice (6 animals per dose) after a single intraperitoneal (i.p.) administration.

The results of these investigations, which clearly support the superiority of the compounds of the formula I according to the invention over the standard preparation naproxen, are collated in Table 2 below.

TABLE 2

| | Antiphlogistic action, ulcerogenity and acute toxicity | | |
|---|---|---|---|
| Compound from example | Adjuvant arthritis (% inhibition at 50 mg/kg p.o.) | Acute ulcerogenity $UD_{50}$ (mg/kg) | Acute toxicity $LD_{50}$ (mg/kg) |
| 1 | 69* | 200 | 600–1200 |
| 2 | 62 | 100 | 600–1200 |
| 3 | 58 | >200 | 600–1200 |
| 4 | 81 | 100–200 | 300–600 |
| 8 | 61* | >200 | 300–600 |
| 9 | 55* | >200 | 600–1200 |
| 10 | 82 | 200 | >1200 |
| 11 | 54 | 100–200 | >1200 |
| 12 | 65 | >200 | 600–1200 |
| 13 | 71 | >200 | 600–1200 |
| 14 | 75 | >200 | 600–1200 |
| 18 | 74 | 100 | >1200 |
| 20 | 72 | 200 | 150–300 |
| 22 | 84* | >200 | 600–1200 |
| naproxen | 55 | 23 | 500 |

*% inhibition at 12.5 mg/kg p.o.

From the dose/action curve in the model of adjuvant arthritis, a $ED_{50}$ value of 6.0 mg/kg, which is clearly more favorable than the corresponding comparison value of 17.5 mg/kg for the standard preparation naproxen, was obtained, for example, for the compound from Example 1. Applied to the acute ulcerogenity, a therapeutic range of about 33 is calculated for the compound of Example 1 by dividing $UD_{50}$ by $ED_{50}$, the therapeutic range being only 1.3 for the comparison preparation naproxen, thus underlining particularly impressively the great importance of the extremely good gastral tolerance of the compounds according to the invention. A likewise clear superiority over the comparison compound is produced when the calculation of the therapeutic range is based on the $LD_{50}$ values determined, and the $LD_{50}/ED_{50}$ quotient is calculated, which is about 150 for the compound of Example 1 and 28.6 for naproxen.

The compounds according to the invention also proved to be clearly superior to the standard preparation naproxen in further specific experiments.

4. Antioxidative action

According to current opinion, aggressive oxygen radicals, which are formed to excess during the chronic inflammation process and, as highly toxic inflammation mediators themselves, perpetually maintain the connective tissue destruction proceeding via irreversible lipid peroxidation of the cell membranes, participate prominently in the progressive course, caused by a number of factors, of rheumatoid arthritis and other inflammatory disorders. As a result, antioxidatively active pharmaceuticals which are capable of deactivating these extremely cytotoxic oxygen radicals should allow specific intervention in the chronic course of the inflammation. A suitable animal model for this type of tissue destruction caused by oxygen radicals is Adriamycin (doxorubicin) induced inflammation in rats.

The investigations were carried out by the method of D. M. Siegel et al. (Inflammation 4 (1980), p. 233) on male Sprague-Dawley rats having a body weight of between 200 and 230 g in groups each with 7 animals, which received 0.1 mg of Adriamycin, dissolved in 0.1 ml of 0.9% strength sodium chloride solution, by subcutaneous injection into the left rear paw. The increase in paw volume after 72 hours was determined by plethysmography measurement as a measure of the degree of inflammation.

The test preparations were administered orally once daily on the 4 successive days, starting with the day of Adriamycin injection, in a 1% strength aqueous carboxymethylcellulose suspension.

As can be seen from Table 3, the compounds from Example 1 and 14, for example, also exhibited a strong, dose-dependent protective effect against Adriamycin-induced tissue destruction in this test. Steroidal and non-steroidal antiphlogistics, including naproxen, are ineffective in this experimental setup.

TABLE 3

| Inhibition of adriamycin-induced inflammation | | | |
|---|---|---|---|
| Animal group | Dose in mg/kg p.o. | Increase in paw volume in $\mu l$ | Protective action in % |
| Control | — | 390 | — |
| Compound from | 25 | 350 | 10 |
| Example 1 | 50 | 120 | 69* |
| Compound from | 25 | 250 | 36 |
| Example 14 | 50 | 160 | 59* |

*Significance p <0.05

5. Inhibition of 5-lipoxygenase

The inhibitory action of the compounds according to the invention of 5-lipoxygenase-catalysed degradation of arachidonic acid was determined, as usual, in in-vitro experiments on isolated polymorphonuclear human granulocytes. To this purpose, the cells were incubated at 37° C. with the particular test preparation and the formation of pro-inflammatory leukotriene $B_4$ ($LTB_4$) was induced after 5 minutes using the calcium ionophor A 23 187 (Calbiochem GmbH, Frankfurt/Main, FRG, Biochemical and Immunochemical Catalog 1985, p. 284). The amount of $LTB_4$ liberated over a period of 10 minutes was determined quantitatively with the aid of a UV detector after separation by means of high-pressure liquid chromatography (HPLC).

As Table 4 below shows, the formation of $LTB_4$, and accordingly the degradation of arachidonic acid via 5-lipoxygenase, could be significantly inhibited by the compounds of the formula I according to the invention in this experimental setup.

TABLE 4

| Inhibition of 5-lipoxygenase | |
|---|---|
| Compound from example | $IC_{50}$ ($10^{-6}$ mol/l) |
| 1 | 9 |
| 3 | 4 |

TABLE 4-continued

| Inhibition of 5-lipoxygenase | |
|---|---|
| Compound from example | IC$_{50}$ (10$^{-6}$ mol/l) |
| 8 | 13 |
| 17 | 10 |

Analgesic action

The analgesic action of the compounds of the formula I according to the invention was tested by means of the acetic acid stretching test on mice by the method of R. Koster et al., Fed. Prod. 18 (1959), p. 412.

The experimental animals used were female mice of a NMRI strain having a body weight (BW) between 21 and 28 g. Groups of 12 animals each received 0.1 ml/10 g of BW of a 0.6% strength acetic acid solution injected intraperitoneally. The test substances were administered 30 minutes beforehand. Immediately after the injection of acetic acid, the animals were placed alone and the number of typical stretching movements occurring within 15 minutes were counted, which comprise a brief tensing of the stomach muscles including the flank parts and subsequent stretching of the rear body and at least one read extremity.

In order to assess the analgesic effect, the number of stretching reactions was compared to those of an untreated control group, those animals which exhibited less than half the average number of stretching movements carried out by the control animals being assessed as relieved of pain. The test substances were administered orally in a volume of 10 ml/kg of BW in a 1% strength aqueous carboxymethylcellulose (CMC) suspension.

The test results in Table 5 below confirm that the compounds of the formula I according to the invention also have a very strong analgesic active component.

TABLE 5

| Analgesic action in the acetic acid stretching test in mice | |
|---|---|
| Compound from example | Animals relieved of pain in % after an oral dose of 158 mg/kg |
| 1 | 83 |
| 2 | 75 |
| 3 | 42 |
| 4 | 83 |
| 8 | 92 |
| 13 | 42 |
| 14 | 67 |
| 22 | 92 |

We claim:

1. A 5-(3-alkyl-5-tert.butyl-4-hydroxyphenyl)-2-amino-6H-1,3,4-thiadiazine of the formula I

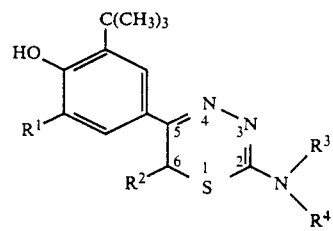

in which

R$^1$ is a straight-chain or branched alkyl group having 1 to 4 carbon atoms,

R$^2$ is a hydrogen atom or an alkyl radical having 1 to 3 carbon atoms,

R$^3$ and R$^4$, independently of one another, represent a straight-chain or branched (C$_1$-C$_6$)alkyl, (C$_3$-C$_6$)-alkenyl or (C$_3$-C$_6$)-alkynyl group which can be substituted by phenyl or halogen, (C$_1$-C$_3$)alkyl- or (C$_1$-C$_3$)alkoxy-substituted phenyl, hnydroxyl or (C$_1$-C$_4$)acyloxy and/or whose C—C sequence may be interrupted by a heteroatom in the form of oxygen or sulfur, it also being possible for one of the two radicals to denote a hydrogen atom, or R$^3$ and R$^4$, together with the nitrogen atom to which they are bound, form a 4- to 7-membered ring which may monosubstituted or polysubstitituted by (C$_1$-C$_4$)alkyl and/or contains, in place of one of the ring carbon atoms, a further heteroatom in the form of oxygen, sulfur or nitrogen to form a pyrrolidine, piperidine, morpholine, thiomorpholine or piperazine ring, it also being possible for the further nitrogen heteroatom of piperazine to carry an alkyl group having 1 to 3 carbon atoms or a phneyl radical in place of hydrogen, or a physiologically acceptable acid-addition salt thereof.

2. A compound as claimed in claim 1, which has at least one of the features that R$_1$ is tert.butyl or methyl or R$^2$ represents hydrogen or methyl or R$^3$ and R$^4$, independently of one another, represent a straight-chain or branched (C$_1$-C$_3$) alkyl or (C$_3$-C$_4$)alkenyl group which may be substituted by optionally substituted phenyl or hydroxyl or whose C—C sequence may be interrupted by an oxygen atom, it also being possible for one of the two radicals to be a hydrogen atom, or R$^3$ and R$^4$, together with the nitrogen atom to which they are bound, form a 5- or 6-membered ring which may be substituted by a (C$_1$-C$_2$)alkyl radical or contains, in place of one of the ring carbon atoms, a further heteroatom in the form of oxygen or nitrogen to form a pyrrolidine, piperidine, morpholine or piperazine ring, it also being possible for the further nitrogen heteroatom of piperazine to carry an alkyl group having 1 to 2 carbon atoms in place of hydrogen.

3. A compound as claimed in claim 1, wherein R$^1$ is a tert.butyl radical and simultaneously R$^2$ represents hydrogen or methyl and R$^3$ and R$^4$, independently of one another, are a straight-chain or branched (C$_1$-C$_3$)alkyl or (C$_3$-C$_4$) alkenyl group which may be substituted by phenyl, it also being possible for one of the two radicals to be a hydrogen atom, or R$^3$ and R$^4$, together with the nitrogen atom to which they are bound, form a piperadine, 4-methylpiperidine, piperazine or 4-methylpiperazine ring.

* * * * *